United States Patent [19]

Larimore

[11] Patent Number: 4,458,696
[45] Date of Patent: Jul. 10, 1984

[54] T.E.N.S. ELECTRODE

[75] Inventor: Franklin C. Larimore, Shoreview, Minn.

[73] Assignee: Minnesota Mining and Manufacturing Company, St. Paul, Minn.

[21] Appl. No.: 203,681

[22] Filed: Nov. 3, 1980

Related U.S. Application Data

[63] Continuation-in-part of Ser. No. 64,576, Aug. 7, 1979, abandoned, which is a continuation-in-part of Ser. No. 22,469, Mar. 21, 1979, abandoned.

[51] Int. Cl.³ .............................................. A61N 1/04
[52] U.S. Cl. ................................... 128/798; 128/640; 128/802
[58] Field of Search .................... 128/639–641, 128/644, 303.13, 783, 798, 802, 803

[56] References Cited

U.S. PATENT DOCUMENTS

| | | | |
|---|---|---|---|
| 3,566,860 | 3/1971 | Moe | 128/2.06 |
| 3,599,629 | 8/1971 | Gordy | 128/2.06 |
| 3,659,614 | 5/1972 | Jankelson | 128/410 |
| 3,865,770 | 2/1975 | Blake | 260/27 R |
| 3,911,906 | 10/1975 | Reinhold, Jr. | 128/2.06 |
| 3,976,055 | 8/1976 | Monter et al. | 128/2.06 E |
| 3,993,049 | 11/1976 | Kater | 128/206 E |
| 3,994,302 | 11/1976 | Brennen | 128/404 |
| 3,998,215 | 12/1976 | Anderson et al. | 128/206 E |
| 4,008,721 | 2/1977 | Burton | 128/418 |
| 4,016,869 | 4/1977 | Reichenberger | 128/2.1 E |
| 4,051,842 | 10/1977 | Hazel et al. | 126/2.06 E |
| 4,054,714 | 10/1977 | Mastrangelo | 428/328 |
| 4,067,342 | 1/1978 | Burton | 128/418 |
| 4,125,110 | 11/1978 | Hymes | 128/2.06 E |
| 4,141,366 | 2/1979 | Cross et al. | 128/418 |
| 4,248,247 | 2/1981 | Ware et al. | 128/802 X |
| 4,273,135 | 6/1981 | Larimore et al. | 128/640 |

FOREIGN PATENT DOCUMENTS

| | | | |
|---|---|---|---|
| 759 | 2/1979 | European Pat. Off. | 128/640 |
| 2814061 | 10/1978 | Fed. Rep. of Germany | 128/783 |
| 2727822 | 1/1979 | Fed. Rep. of Germany | 128/803 |

Primary Examiner—Lee S. Cohen
Attorney, Agent, or Firm—Donald M. Sell; James A. Smith; Carolyn A. Bates

[57] ABSTRACT

A T.E.N.S. electrode is disclosed comprising an essentially dry, body-conformable, electrically-conductive interfacing layer having a maximum thickness of 10 mils, a low profile, one-piece electrically-conductive connector adherent to the top surface of the interfacing layer and a backing member, overlying the interfacing layer and the connector. The electrode is extensible in at least one direction up to 50 percent and requires less than about $25 \times 10^6$ dynes/cm² for an elongation of 20 percent as tested per ASTM Standard D-882.

8 Claims, 8 Drawing Figures

T.E.N.S. ELECTRODE

RELATED APPLICATIONS

This application is a continuation-in-part of co-pending application Ser. No. 64,576 filed Aug. 7, 1979, now abandoned, which is a continuation-in-part of application Ser. No. 22,469, filed Mar. 21, 1979, now abandoned.

TECHNICAL FIELD

This invention relates to the field of "dry", disposable biomedical electrodes. More particularly, it relates to dry, disposable biomedical electrodes for transcutaneous electrical nerve stimulation.

BACKGROUND ART

Transcutaneous electrical nerve stimulation (T.E.N.S.) is a procedure in which an electrical signal is transmitted through the skin to appropriate underlying nerves where it helps prevent pain signals from reaching the brain. T.E.N.S. has been used for about ten years in major hospitals, medical schools and pain clinics with good results. It is a very desirable method of pain control because it is safe, effective, non-invasive, non-narcotic and has no known side effects.

T.E.N.S. requires the placement of an electrode on the body at the site of stimulation to deliver the electrical signal to the skin beneath the electrode. Typically, the electrode will consist of a connector having means for attachment of a lead wire and a relatively flat, body-conformable, electrical impulse-distribution portion. Metallic foils or conductive plastics are commonly used to fabricate the connector. The connector is attached via the lead wire to a stimulator. To enhance electrical conductivity between the connector and the skin and to reduce the likelihood of "hot spots" developing, a conformable, electrically-conductive interface material is applied between the skin and the connector. The traditional interface material is a conductive gel or a pad saturated with a conductive gel. The gel or gel pad is applied to the skin and overlaid with the connector. An adhesive patch is generally required to hold the electrode in place. This type of electrode assembly suffers from a number of disadvantages. Firstly, conductive gels are predominately water and tend to dry out within a relatively short time after application to the skin and lose their conductivity. This necessitates removal of the electrode and re-application of gel on a daily basis. Secondly, the skin often becomes irritated from the repeated removal of the adhesive patch holding the electrode in place.

These problems were alleviated somewhat by replacing gel with a dry, electrically-conductive interface material, such as plasticized karaya gum, which does not dry out during use. However, karaya gum pads have low adhesion, and an adhesive patch is sometimes required to hold the electrode assembly on the skin. The adhesive patch restricts the movement of the underlying skin and causes a great deal of discomfort to the wearer over prolonged periods of use. Since T.E.N.S. is used for the management of chronic pain, prolonged application of an electrode, e.g., two to seven days, is desirable.

The need has developed for a disposable T.E.N.S. electrode which (1) is economical; (2) does not dry out during use; (3) is self-adhering; and (4) is extensible with the skin.

The prior art has provided T.E.N.S. electrodes meeting one or more of the aforementioned criteria, but has been unsuccessful in providing an electrode meeting all of them. For example, U.S. Pat. Nos. 4,008,721, 4,067,342 and 4,141,366 disclose dry, self-adhering stimulating electrodes wherein the interface layers are pressure-sensitive adhesive materials rendered conductive by the inclusion of conductive metallic particles. These electrodes contain non-woven fabric backings which limit the ability of the electrodes to move with the skin.

U.S. Pat. No. 4,066,078 discloses stimulating electrodes wherein the interface material is an electrically-conductive adhesive comprising certain organic polymers plasticized with a polyhydric alcohol. In the electrode described in U.S. Pat. No., 4,125,110, the conductive interface material is a mixture of a natural organic polysaccharide, such as karaya gum, and a polyhydric alcohol. The interfacing layers in the aforementioned two electrodes are bonded to a metallic foil. The foil is not extensible and restricts the extensibility of the interfacing layer. Furthermore, the interfacing layer in both electrodes is quite thick and too costly to provide a practical, low-cost disposable T.E.N.S. electrode.

The T.E.N.S. electrode of the present invention provides a combination of desirable features heretofore unavailable. In addition to having a "dry" conductive interface layer, which can be used for a period of days without drying out, the thickness of the layer is kept at a minimum to provide a low-cost, disposable electrode. The unique backing layer of the electrode, in combination with the interface layer and the low profile connector, provide an extensible electrode that stretches with the skin and can be worn for long periods, without discomfort or irritation, even over skin areas undergoing constant stretching, e.g., lower back.

DESCRIPTION OF THE INVENTION

According to the present invention, there is provided a T.E.N.S. electrode comprising a dry bodyconformable, electrically-conductive interfacing layer having a maximum thickness of about 10 mils (254 micrometers). The interfacing layer has an adherent top surface and a lower body-contacting surface adapted for adherence to the skin. For connecting the electrode to an electrical stimulator, there is provided a one-piece, body-conformable electrically-conductive connector having a substantially flat electrical impulse-distribution protion, the lower surface of which is adhered to the top surface of the interfacing layer. The upper surface of the connector has means for connection to an electrical stimulator. A backing member is preferably adhered to the upper surface of the interfacing layer to enhance the mechanical integrity of the electrode. It is also preferred that the backing cover all or a portion of the top surface of the connector to prevent displacement of the connector from the interfacing layer during use. When the backing member is adhered to a substantial portion of the upper surface of the connector to hold it in place on the interfacing member, lateral access for connection with the stimulator is provided, or the backing may have a hole therethrough allowing access for the lead wire. The T.E.N.S. electrode of the present invention is extensible in at least one direction up to 50 percent and requires less than about $25 \times 10^6$ dynes/cm$^2$ for an elongation of 20% as tested per ASTM standard D-882.

DESCRIPTION OF THE PREFERRED EMBODIMENT

Figure 3:
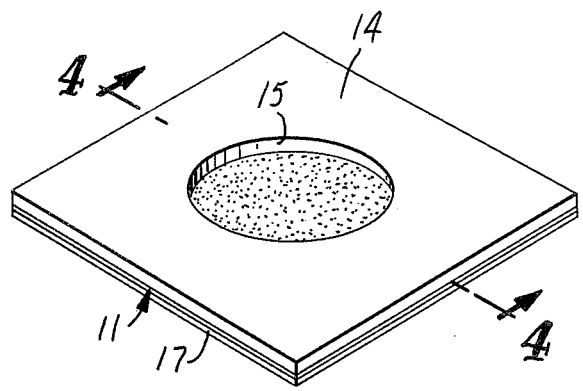
FIG. 3 is a perspective view of the interfacing layer and attached backing of the electrode of FIG. 1.
Figure 1:
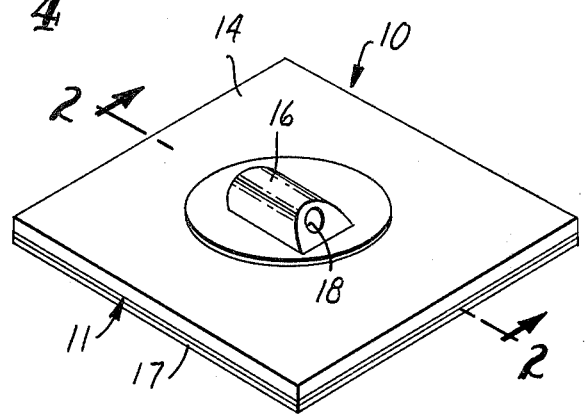
FIG. 1 is a perspective view of one embodiment the T.E.N.S. electrode of the present invention.

Referring to the drawing wherein like reference characters designate like or corresponding elements and referring particularly to FIG. 1, the T.E.N.S. electrode 10 is comprised of a one-piece electrically-conductive connector 16 and a dry, body-conformable, electrically-conductive interfacing layer 11 having a top surface and a lower body-contacting surface adapted for adherence to the skin.

Interfacing layer 11 is thin, i.e., 10 mils (254 micrometers) or less, and preferably 3 to 7 mils (76–178 micrometers). It also exhibits extensibility which is similar to skin. Extensibility is used herein to mean the ability to stretch in at least one direction in a manner which is similar to human skin. Skin is a very extensible material which stretches 20% to 30% during normal activities and up to 50% if needed. Skin is also resilient which allows it to return to an unstretched condition when stress is removed. The preferred interfacing layer 11 is comprised of a carrier portion 12, coated with an electrically conductive adhesive 13. Carrier portion 12 may be comprised of a mat of separate fibers bonded together, e.g. a nonwoven web, which is body-conformable and extensible. The fibers may be polyester, nylon or a cellulosic derivative, e.g., rayon, paper, etc. Carrier portion 12 may also be of a woven structure if the weave allows for the needed extensibility and adhesive impregnation. The ability of a woven or nonwoven structure to allow for impregnation of the conductive adhesive enables the adhesive 13 to conduct the electrical impulse evenly throughout the interfacing layer 11. The preferred material for carrier portion 12 is Crystex ™ paper tissue, manufactured by Crystal Paper Co., Middletown, Ohio. Carrier portion 12 imparts a measure of mechanical strength to the construction and may be omitted if the conductive adhesive layer 13 has sufficient strength and extensibility to maintain integrity during use.

In addition to being electrically-conductive, adhesive 13 should exhibit sufficient tack to adhere to the skin. The preferred adhesive 13 is comprised of 75:25 butyl acrylate-acrylic acid copolymer neutralized to 95 mole percent with methyl diethanolamine to which 20 parts/100 parts copolymer and 30 parts/100 parts copolymer of a water-soluble plasticizer and a water-soluble tackifier, respectively, are added as described in U.S. Pat. No. 3,065,770. The resultant adhesive composition preferably is coated onto both sides of the carrier portion 12 at 9.2 micrograms/cm$^2$ (dry basis) to form the interfacing layer 11.

It is contemplated that other polymeric adhesives such as those disclosed in U.S. Pat. Nos. 4,067,342, 3,911,906, 4,054,714 and 3,994,302 may be utilized in interfacing members of the present invention.

Optionally attached to the top surface of interfacing layer 11 is a backing member 14 which, in the embodiment of FIGS. 1-4, has a hole 15 therethrough which allows access to the top surface of the interfacing layer 11. The backing member 14 acts to maintain the integrity of the interfacing layer 11 by covering all of its surface except the hole 15 when the electrode 10 is positioned on the wearer. Backing member 14 must exhibit sufficient extensibility to be complaint with interfacing layer 11 after electrode 10 is placed on the wearer. The preferred material for backing member 14 is a vinyl foam tape sold under the trade name of "Microfoam" Tape, 3M Company, St. Paul, Minnesota 55101. Other suitable materials which may be used to form the backing member include a compressed polyurethane foam sold under the trade name of "Scott Felt", Scott Foam Division, Scott Paper Company, Eddystone, Pennsylvania or a closed cell polyethylene foam, sold under the trade name of "Volara", Voltex Corporation, Lawrence, Massachusetts.

Backing member 14 may be omitted resulting in a biomedical electrode constituted of the interfacing layer 11 and body-conformable connector 16 (discussed below). With this alternative construction, it is preferable that connector 16 cover the entire top surface of interfacing layer 11 to prevent foreign matter from adhering to the top surface of the interfacing layer 11.

For the present invention, a body-conformable, one-piece electrically conductive connector 16 connects the interfacing layer 11 to the electrical stimulator. Connector 16 is comprised of a substantially flat electrical impulse distribution portion having a flat lower surface adapted to fit within hole 15 of backing member 14 in electrical contact with the interfacing layer 11. Connector 16 also is provided with an upper surface having an adapter 18 for connection to the connector lead of an electrical stimulator (not shown). The connector is preferably made of a carbon-impregnated silicone rubber (Silicone Rubber Compound C-968, SWS Silicones Corporation, Adrian, Michigan 49221). Other suitable carbon-impregnated polymeric materials include plasticized polyvinyl chloride, epichlorohydrin rubber, polyurethane molding compound, polytetrafluoroethylene and a polymer of ethylene-propylene-diene (e.g. EPDM rubber).

If the backing layer 14 is omitted from the electrode and the connector covers substantially the entire upper surface of the interfacing layer, the connector must have sufficient extensibility to enable the electrode to achieve the requisite extensibility, i.e., up to 50 percent elongation in one direction and requiring less than about $25 \times 10^6$ dynes/cm$^2$ for elongation of 20% as tested in ASTM standard D-882.

An additional feature of connector 16 is that it is releasably attached to interface layer 11 and can be reused.

Figure 4:
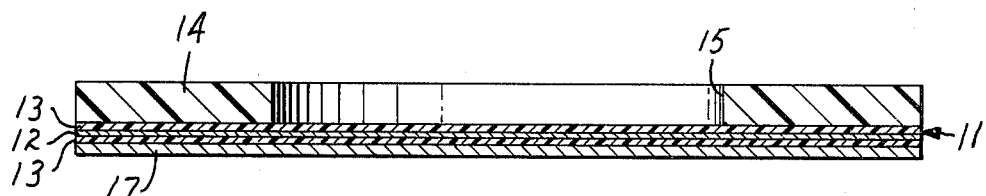
FIG. 4 is a cross-sectional view of the electrode of FIG. 3 through line 4—4.
Figure 2:
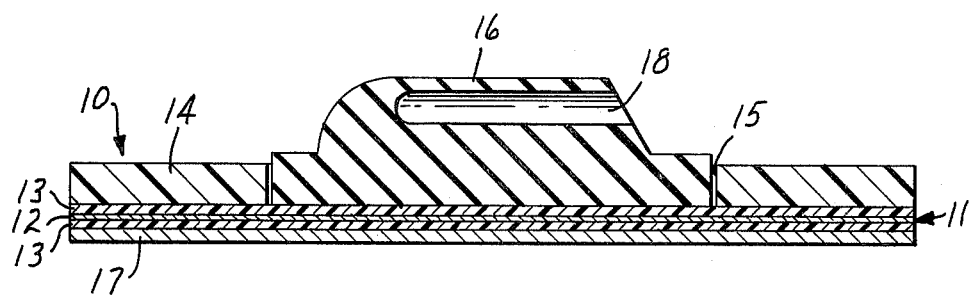
FIG. 2 is an enlarged cross-sectional view of the electrode of FIG. 1 through line 2—2.

Referring to FIG. 4, an optional release liner 17 may be attached to the lower surface of the interfacing layer 11 in order to preserve its adhesive character until it is ready for use. Such release liners are well known to the art.

To use the biomedical electrode assembly of the present invention, the release liner 17 is removed and the electrode is placed on the desired surface of the skin. Prior to placing the electrode to the skin, the skin or the lower surface of the interfacing layer 11 may be wetted with water to optimize the adherence and conductivity of the adhesive. The connector, which has been previously attached to the lead of the electrical stimulator, is then releasably adhered to the upper surface of the interfacing layer 11 through hole 15. When stimulation is complete, the connector is removed and may be preserved, while the disposable portion comprising the interfacing layer 11 and the attached backing 14 may be discarded.

Referring to FIGS. 5 through 8, alternative embodiments 20 and 30 may be made without departing from the spirit of the present invention. The alternative embodiments 20 and 30 are also comprised of an optional release liner 17, an interfacing layer 11 and an optional backing member 14A. Connectors 21 and 31 of embodiments 20 and 30, respectively, likewise comprise a one-piece construction having means for connection with an electrical stimulator 18 and a flat electrical impulse distribution portion for electrical contact with interfacing layer 11.

Connectors 21 and 31 differ from connector 16 of electrode 10 in that they are elongated rather than circular. It has been found that in certain use situations, movement of the patient may cause the connector 16 of embodiment 10 to become separated from interfacing layer 11. By overlaying a portion of backing 14A on the top surface of connector 21 or 31 this problem is substantially eliminated.

Figure 5:
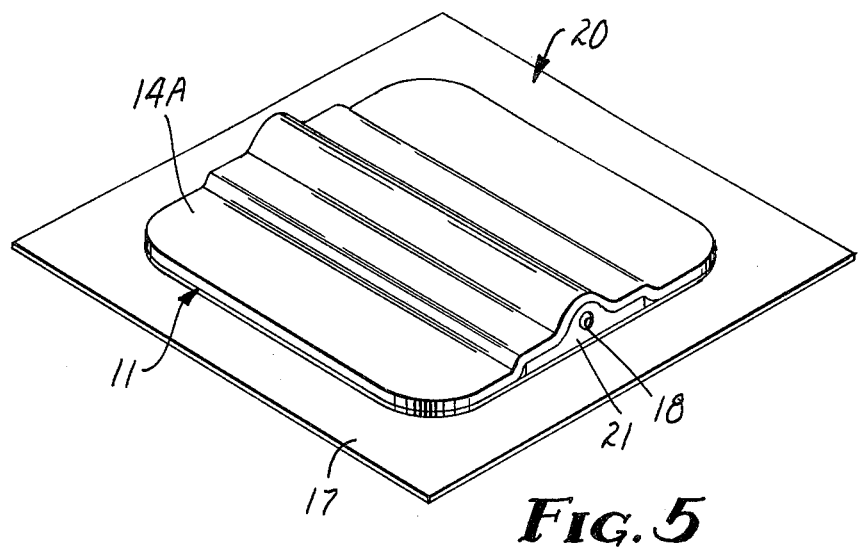
FIG. 5 is a perspective view of an alternative embodiment of the electrode of the present invention.
Figure 6:
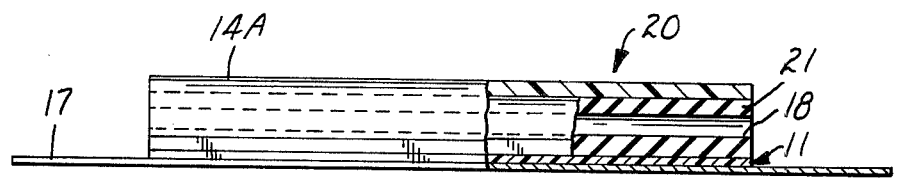
FIG. 6 is a fragmented side view of the electrode of FIG. 5.
Figure 7:
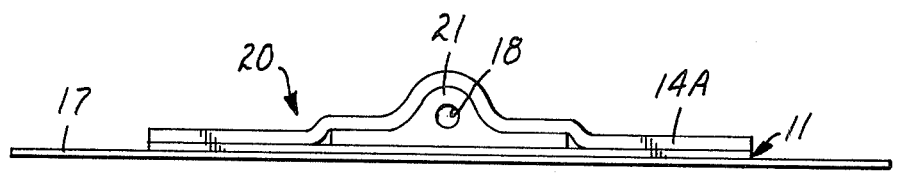
FIG. 7 is an end view of the electrode of FIG. 6.
Figure 8:
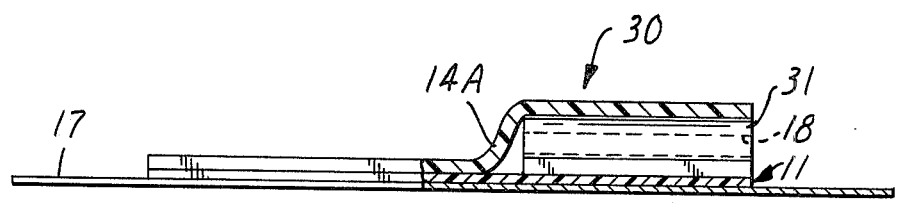
FIG. 8 is a side view of a second alternative embodiment of the electrode of the present invention.

In order to facilitate the placement of connector 21 or 31, an additional double-sided release liner (not shown) may be placed between a portion of the backing member 14 and the interfacing layer 11. This double-sided release liner may then be removed and connector 21 or 31 positioned on interfacing layer 11 as shown in FIG. 5 or 8. Backing member 14A is then positioned so as to releasably adhere to at least a portion of the top surface of connector 21 or 31 and interfacing layer 11 so as to insure electrical contact between connector 21 or 31 and interfacing layer 11.

Electrode 20 as shown in FIG. 5 is the presently preferred embodiment of the T.E.N.S. electrode of the invention. The top surface of connector 21 is completely covered by backing member 14A. The connector may be removed, if desired, after the initial use for later reuse, but it is contemplated that, in most cases, the entire electrode will be discarded after removal from the body.

It has been found that when electrodes of the invention are applied to the skin, both the underlying skin and the overlying electrode are extended by the same forces acting upon the skin. Since the electrode stretches with the skin, stress and strain on the skin is so insignificant as to be virtually unnoticeable. A dramatic reduction in discomfort and irritation is possible over prior art T.E.N.S. electrodes.

Elongation relaxation tests were run on human skin utilizing methods described in the book by R. M. Kenedi, T. Gibson and C. H. Daly "Structure and Function of Connective and Skeletal Tissue", London: Butterworths 1965 at page 388. It was found that when the skin was retained in a stressed condition, it exhibits a relaxation whereby the force required to maintain the same stress condition gradually declines. Test runs on electrodes of the present invention in accordance with ASTM test D-882 indicate that for an electrode to have elongation and relaxation properties similar to skin, it must preferably (1) be extensible in at least one direction up to 50 percent and (2) require less than about $25 \times 10^6$ dynes/cm$^2$ for an elongation of 20%. Furthermore, it should exhibit a stress relaxation with time when elongated 20% of from about 10% to 20% after 1 minute and about 20% to about 50% after 10 minutes. The electrodes of the present invention exhibit this stress relaxation with time and have sufficient relaxation properties to recover to near their original unstressed length when all stress is removed.

The preferred embodiment of the electrode of the invention as illustrated in FIG. 5 (constructed of the preferred materials described hereinabove) was tested (with release liner 17 removed) according to ASTM test D-882. The results are set forth in the following Tables I and II.

Preferred Construction

TABLE I*

| Elongation | FORCE | | | |
|---|---|---|---|---|
| | P.S.I. | DYNES/cm$^2$ × 10$^6$ | LBS/IN WIDTH | DYNE/cm × 10$^4$ |
| 5% | 26.86 | 1.85 | 0.94 | 16.46 |
| 10% | 32.29 | 2.23 | 1.13 | 19.78 |
| 20% | 41.14 | 2.84 | 1.44 | 25.21 |

Stress relaxation results were as follows at 20% elongation

TABLE II*

| TIME | P.S.I. | (D/cm$^2$ × 10$^6$) | LBS/IN WIDTH | (D/cm × 10$^4$) | DECREASE |
|---|---|---|---|---|---|
| 0 | 41.14 | 2.84 | 1.44 | 25.21 | |
| 1 min | 15.43 | 1.06 | 0.54 | 9.45 | 62% |

*The two flat sides of the electrodes (as contrasted to the sides having the exposed connector) were inserted into the jaws of the "Instron" machine.

What is claimed is:

1. A T.E.N.S. electrode comprising:
  an essentially dry, body-conformable, electrically-conductive interfacing layer having an adherent top surface and a lower body-contacting surface adherent to the skin, said interfacing layer being extensible up to 50 percent in a manner similar to human skin;
  a backing member attached to said top surface of said interfacing layer, said backing member having a hole therethrough providing access to said interfacing layer for electrical contact, said backing member exhibiting sufficient extensibility to be compliant with said interfacing layer after the electrode is placed on the wearer; and
  a body-conformable, one-piece electrically-conductive connector having a substantially flat electrical impulse distribution portion releasably adhered in electrical contact with said top surface of said interfacing layer through said hole of said backing member in electrical contact with said interfacing layer and an upper surface having therein a means for releasable connection to a connector lead of an electrical stimulator.

2. A T.E.N.S. electrode comprising:
  an essentially dry, body-conformable, electrically-conductive interfacing layer having an adherent top surface and a lower body-contacting surface adherent to the skin, said interfacing layer being extensible up to 50 percent in a manner similar to human skin;

a body-conformable, one-piece electrically-conductive connector having a substantially flat electrical impulse distribution portion adhered in electrical contact with said top surface of said interfacing layer and an upper surface having therein means for releasable connection to a connector lead of an electrical stimulator; and a backing member adhered to said connector and at least a portion of said top surface of said interfacing layer whereby said connector is retained in electrical contact with said interfacing layer, said backing member exhibiting sufficient extensibility to be compliant with said interfacing layer after the electrode is placed on the wearer.

3. The electrode in accordance with claims 1 or 2 wherein said connector consists of a carbon-impregnated polymeric material selected from the group consisting of silicone rubber, plasticized polyvinyl chloride, epichlorohydrin rubber, polytetrafluoroethylene, or a polymer of ethylene-propylene diene.

4. The electrode in accordance with claims 1 or 2 wherein said interfacing layer comprises a carrier portion having an electrically conductive adhesive at said top surface and said lower body-contacting surface.

5. The electrode in accordance with claim 4 wherein said carrier portion is a non-woven web.

6. The electrode in accordance with claim 4 wherein said adhesive is butyl acrylate-acrylic acid copolymer neutralized with methyl diethanolamine.

7. The electrode in accordance with claim 6, wherein the mole ratio of butyl acrylate to acrylic acid is 75:25 and said copolymer is neutralized to 95 mole percent with diethanolamine.

8. The electrode according to claim 2 wherein said backing member is a vinyl foam.

* * * * *